US009913722B2

(12) United States Patent
Segina et al.

(10) Patent No.: US 9,913,722 B2
(45) Date of Patent: Mar. 13, 2018

(54) PERIPROSTHETIC FRACTURE MANAGEMENT ENHANCEMENTS

(71) Applicant: Genesis Medical Devices LLC, Indialantic, FL (US)

(72) Inventors: Daniel Nick Segina, Satellite Beach, FL (US); James A. Proctor, Jr., Indialantic, FL (US); James Arthur Proctor, III, Indialantic, FL (US)

(73) Assignee: Genesis Medical Devices LLC, Indialantic, FL (US)

( * ) Notice: Subject to any disclaimer, the term of this patent is extended or adjusted under 35 U.S.C. 154(b) by 0 days.

(21) Appl. No.: 15/372,609

(22) Filed: Dec. 8, 2016

(65) Prior Publication Data

US 2017/0151059 A1    Jun. 1, 2017

Related U.S. Application Data

(63) Continuation of application No. 15/068,923, filed on Mar. 14, 2016, now Pat. No. 9,522,066, which is a (Continued)

(51) Int. Cl.
*A61F 2/38* (2006.01)
*A61F 2/28* (2006.01)
(Continued)

(52) U.S. Cl.
CPC ........ *A61F 2/3609* (2013.01); *A61B 17/1725* (2013.01); *A61B 17/1728* (2013.01);
(Continued)

(58) Field of Classification Search
CPC .. A61F 2/28; A61F 2/3859; A61F 2/32; A61F 2/36; A61F 2/3601; A61F 2/3609;
(Continued)

(56) References Cited

U.S. PATENT DOCUMENTS 6,494,913 B1    12/2002   Huebner
8,062,378 B2    11/2011   Fonte
(Continued)

*Primary Examiner* — Jason-Dennis Stewart
(74) *Attorney, Agent, or Firm* — VLP Law Group, LLP

(57) ABSTRACT

The present invention provides for a variety of fracture fixation options should a fracture occur after total hip arthroplasty or total knee arthroplasty, and provides associated methods and apparatus for application of provided fixation. The ability to pre-engineer fracture fixation contingent solutions into femoral or tibial components provides for a distinct clinical advantage in the planning and execution for periprosthetic fracture fixation. Said methods and apparatus include targeting devices which allow for intimate association of fixed angle locking screws in pre-drilled holes in an existing prosthetic, femoral nail, or other components including additional fixation components. Use of pre-engineered fracture fixation contingent solutions into femoral or tibial components provides for a distinct clinical advantage in the planning and execution for periprosthetic fracture fixation. Such apparatus and methods further include the use of alignment devices and other components to allow for ease of repair of periprosthetic fractures utilizing the pre-engineered solutions. Such targeting devices are required in specific circumstances as the prosthetics may prevent x-ray imaging and consequently free hand alignment.

22 Claims, 18 Drawing Sheets

Related U.S. Application Data continuation of application No. 14/200,678, filed on Mar. 7, 2014, now Pat. No. 9,345,523, which is a continuation of application No. 13/398,512, filed on Feb. 16, 2012, now Pat. No. 8,709,092.

(60) Provisional application No. 61/443,292, filed on Feb. 16, 2011.

(51) Int. Cl.
| | | |
|---|---|---|
| *A61F 2/36* | (2006.01) | |
| *A61B 17/17* | (2006.01) | |
| *A61B 17/80* | (2006.01) | |
| *A61F 2/30* | (2006.01) | |
| *A61B 17/72* | (2006.01) | |

(52) U.S. Cl.
CPC ...... *A61B 17/8061* (2013.01); *A61F 2/30771* (2013.01); *A61F 2/389* (2013.01); *A61F 2/3859* (2013.01); *A61B 17/72* (2013.01); *A61F 2/3607* (2013.01); *A61F 2002/3082* (2013.01); *A61F 2002/3085* (2013.01); *A61F 2002/30517* (2013.01); *A61F 2002/30772* (2013.01); *A61F 2002/3652* (2013.01)

(58) Field of Classification Search
CPC ..... A61F 2/389; A61B 17/80; A61B 17/8061; A61B 17/1725; A61B 17/1728
See application file for complete search history.

(56) References Cited

U.S. PATENT DOCUMENTS

| | | |
|---|---|---|
| 8,236,005 B2 | 8/2012 | Meneghini et al. |
| 2007/0005146 A1 | 1/2007 | Heyligers et al. |
| 2007/0225819 A1 | 9/2007 | Eva |
| 2008/0255560 A1 | 10/2008 | Myers et al. |
| 2009/0043395 A1 | 2/2009 | Hotokebuchi et al. |
| 2010/0262194 A1 | 10/2010 | Wagner et al. |
| 2010/0318086 A1 | 12/2010 | Winemaker |
| 2011/0137314 A1 | 6/2011 | Kuster et al. |
| 2011/0196491 A1 | 8/2011 | Huebner |
| 2011/0313532 A1 | 12/2011 | Hunt |

PERIPROSTHETIC FRACTURE MANAGEMENT ENHANCEMENTS

RELATED APPLICATION

This application is a continuation of U.S. patent application Ser. No. 15/068,923 filed on Mar. 14, 2016 by Daniel Nick Segina, James A. Proctor, Jr. and James A. Proctor, III for PERIPROSTHETIC FRACTURE MANAGEMENT ENHANCEMENTS, which is a continuation of U.S. patent application Ser. No. 14/200,678 filed on Mar. 7, 2014 by Daniel Nick Segina, James A. Proctor, Jr. and James A. Proctor, III for PERIPROSTHETIC FRACTURE MANAGEMENT ENHANCEMENTS, which is a continuation of U.S. patent application Ser. No. 13/398,512 filed on Feb. 16, 2012, by Daniel Nick Segina, James A. Proctor, Jr. and James A. Proctor, III for PERIPROSTHETIC FRACTURE MANAGEMENT ENHANCEMENTS, which claims the benefit of U.S. Provisional Application No. 61/443,292, filed on Feb. 16, 2011.

The entire teachings of the above applications are incorporated herein by reference.

BACKGROUND OF THE INVENTION

1. Field

The present disclosure relates generally to methods and apparatus for allowing for improvements in the repair of Periprosthetic fractures. In some embodiments, these improvements the inclusion of features within the implanted parenthesis allowing for use of an apparatus for effective and efficient alignment and installation of one or more fracture stabilization components and related components.

2. Related Art

The current state of fixation of periprosthetic fracture revolves around devices that are designed to avoid originally placed femoral or tibial components. With a multitude of different fracture patterns that could clinically exist, current solutions for the variability of fracture patterns revolve around the use of either an external bone plate or an internal medullary rod/nail.

The foregoing describes approaches for conventional periprosthetic fracture management. Such approaches often result in sub-optimal prognosis as compared with fracture management in the absence of a conventional prosthesis. Additional impacts to the patient recovery time result from significantly more invasive procedures being required for the application of such conventional fracture management devices.

SUMMARY OF THE INVENTION

Embodiments of the current invention provide for pre-engineered fracture fixation contingent solutions into femoral or tibial components, resulting in a distinct clinical advantage in the planning and execution for periprosthetic fracture fixation. Additional embodiments include a pre-engineered solution to intimately associate with the previously placed total hip arthroplasty or total knee arthroplasty and further in some embodiments utilize approaches for allowing targeting of required fasteners, screws and the like, using a mechanically associated relationship to the existing prosthetic, or other components.

Specific embodiments of this invention are related to the design of prosthetics for artificial hip and knee replacement, the repair of Periprosthetic fractures, and associated methods and apparatus for use in the application of fracture stabilization components. Additional embodiments provide for a variety of fracture fixation options should a fracture occur after total hip arthroplasty or total knee arthroplasty.

To support the application of such fixation options in specific embodiments provide for apparatus and methods to include the use of alignment devices and other components to allow methods for ease of repair of Periprosthetic fractures utilizing the pre-engineered solutions. Such targeting devices are required in specific circumstances as the prosthetics may prevent x-ray imaging and consequently free hand alignment. Specific embodiments of the aforementioned alignment device/outrigger may be composed of carbon fiber or other materials transparent to imaging technology utilizing radio lucent materials.

In one embodiment, a method for repairing a periprosthetic fracture comprises mounting an aligning device in mechanical registration with an in situ prosthetic component and locking a fracture stabilization component, and aiming arm, the aligning device and the in situ prosthetic component in mechanical alignment, utilizing the aiming arm to provide alignment of one or more mechanical cannula with one or more prosthetic component interfaces and securing one or more bone fracture segments associated with the periprosthetic fracture with said fracture stabilization component using screws, wherein the fracture stabilization component and the prosthetic component are further mechanically secured.

In another embodiment, a periprosthetic fracture device comprises mounting an aligning device in mechanical registration with an in situ prosthetic component and locking a fracture stabilization component, and aiming arm, the aligning device and the in situ prosthetic component in mechanical alignment, utilizing the aiming arm to provide alignment of one or more mechanical cannula with one or more prosthetic component interfaces and securing one or more bone fracture segments associated with the periprosthetic fracture with said fracture stabilization component using screws, wherein the fracture stabilization component and the prosthetic component are further mechanically secured.

In another embodiment, the prosthetic component further comprises a threaded coupling point for receiving the aligning device.

In another embodiment, the prosthetic component further comprises a guide wire.

In another embodiment, the aligning device and the aiming arm are a single component.

In another embodiment, the prosthetic component is a modified femoral component, and wherein said femoral component interfaces with a periprosthetic distal femoral polyaxial locking plate.

In another embodiment, the prosthetic component is a modified tibial tray component.

The method of Claim 1, wherein the component interface is notched or keyed for proper rotational alignment.

In another embodiment, the mechanical registration is a notched mechanical interface between a femoral nail and the prosthetic component.

In another embodiment, the aligning device and the aiming arm are mechanically assembled components.

In another embodiment, the fracture stabilization component comprises one of the following: a femoral nail, tibial nail, femoral plate, or tibial nail.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Figure 1:
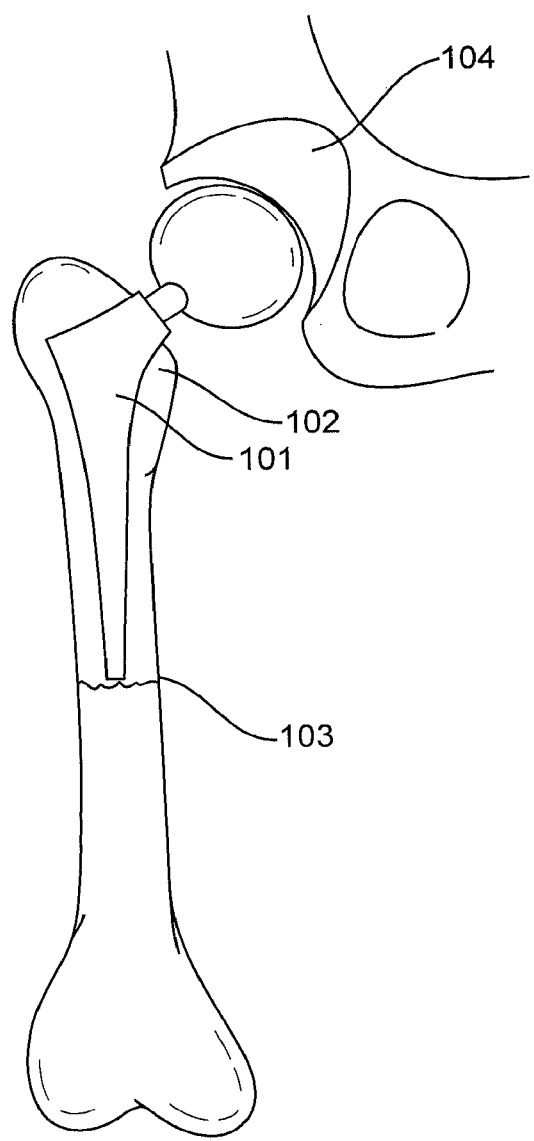
FIG. 1 is an illustration of a first defined fracture below the hip prosthesis.

FIG. 1: Problem #1—Fracture Below Hip Prosthesis

FIG. 1 shows an existing problem in the industry of a fracture below a hip prosthesis. The prosthesis 101, articulates with the hip joint 104, as is known within the industry. Furthermore, the Hip Prosthesis 101 is implanted within the proximal femur 102. Periprosthetic Femur fracture 103 occurs post implantation of the prosthesis 101, into the proximal femur. The current challenge within orthopedic surgery is the fixation of a fracture after implantation of Hip Prosthesis 101. The metallic implant obscures the capacity to provide for fixation through the bone by occupying the inner space of the medullary femoral canal. Clinical solutions attempt to avoid the femoral prosthesis 101 by providing for screw trajectories away from the implant or options for circumferential wire fixation around the implant. While the current fracture pattern 103 is described within, this does not and is not intended to limit the scope of the application of the embodiments of this invention.

Figure 2:
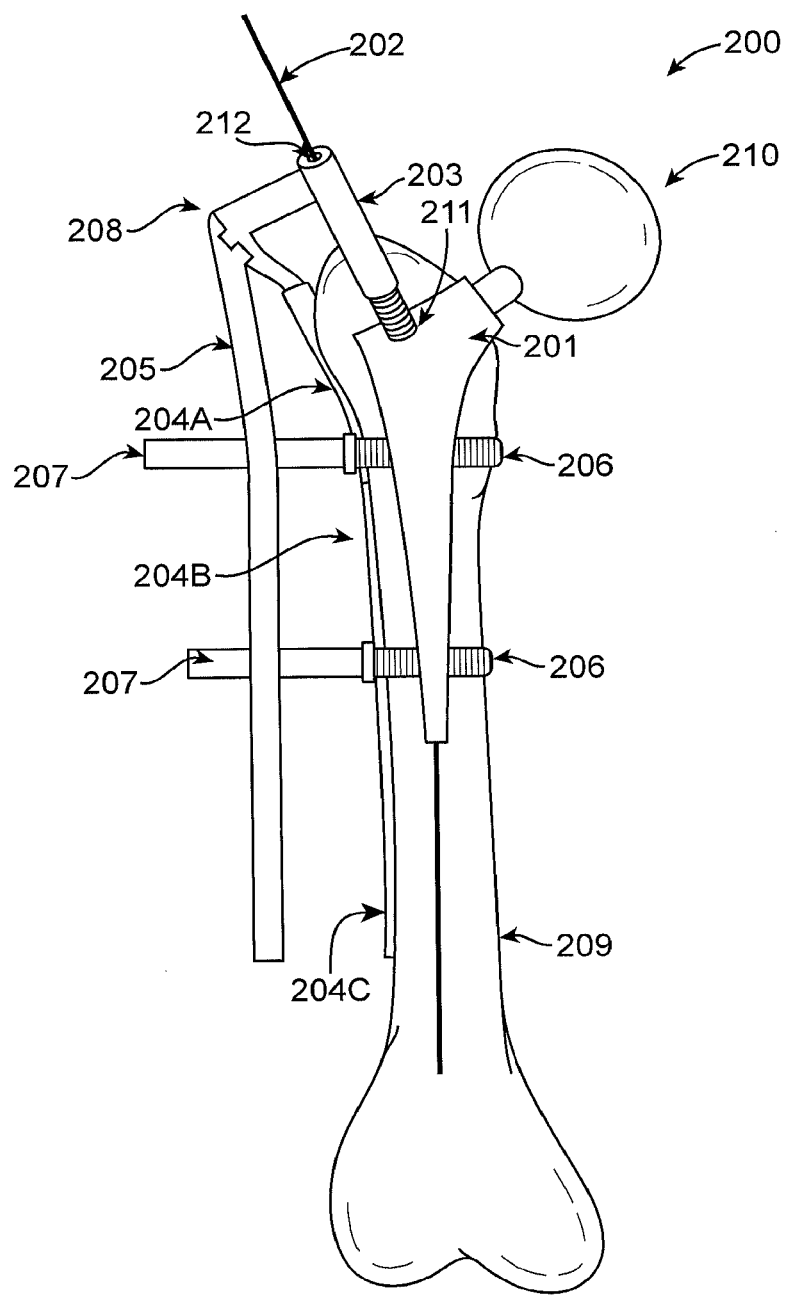
FIG. 2 is an illustration of an embodiment including: Modified Femoral Component to Accommodate Cannulated Outrigger, Custom Modular Plate and Targeting Device.

FIG. 2: Embodiment of Solution #1—Modified Femoral Component to Accommodate Cannulated Outrigger, Custom Modular Plate and Targeting Device.

This section discusses one embodiment to address the problem of FIG. 1, depicted in fracture pattern 103.

Modified Femoral Component 201 is implanted into the proximal femur.

Femoral component 201 with hollow core 212 to accommodate guide a Targeting Guide Wire 202 is depicted to provide for a reference point for an aligning device, such as Cannulated Outrigger 203. This allows for alignment and an intimate association between Femoral Component 201 and an aligning device, such as Cannulated Outrigger 203, resulting in a unique interface reference point 211. Interface Reference point 211 may utilize keyed interfaces between an aligning device, such as Cannulated Outrigger 203 and between Femoral Component 201 so as to allow for a further angular or rotational reference. As a result, spatial orientation is now predetermined and referenced off of the previously implanted Femoral Component 201. With a fracture stabilization component, such as the Cannulated Outrigger 203 mated to Modified Femoral Component 201, an aiming arm, such as a Distal Targeting Device 205 can then be assembled to provide for appropriate and accurate targeting of Fixed Angled Locking Screws 206; targeting through Screw Alignment Cannulae 207 thus providing a mechanism for security fixation of a fracture stabilization component, such as the Custom Modular Plate 204A, 204B, and 204C. Clinical solutions for Coupling Point 208 represent a mating mechanism between the Cannulated Outrigger 203 and an aiming arm, such as the Distal Targeting Device 205. This intimate fit, once again, assures appropriate targeting of the Fixed Angled Locking Screws 206 through the Modified Femoral Component 201 which revolves around fixation. The Modified Femoral Component 201 is implanted into the Native Femur depicted as 209. The interface between Modified Femoral Component 201 and Cannulated Outrigger 203 is described via a threaded Cannulated Outrigger Interface 211. The cannulation of this interface happens over a hollow core 212 which is inserted through Cannulated Outrigger 203 and the Modified Femoral Component 201.

The capacity for the Modified Femoral Outrigger 203 to be mated to the Femoral Component 201 provides for accurate reference point to thus target the screws depicted in 206. This overcomes the challenge of alignment, which is not referenced, and presents a difficult clinical challenge for targeting the appropriate screw 206 and implant 201 interfaces. The clinical benefits extend to the decreased surgical time due to known reference point between Modified Femoral Component 201 and 203; in addition to decreased surgical trauma and surgical dissection in attempts to find the appropriate alignment between Modified Femoral Component 201, Plate 204A, B, and C, and Screw 206. The capacity to limit surgical time as well as surgical exposure necessarily translates into decreased cost as well as decreased patient morbidity. Additionally, improved mechanical fixation would be enhanced due to accurate targeting and interface between Modified Femoral Component 201 and a fracture stabilization component, such as Modular Plate 204A, B, and C as well as Screws 206. Femoral Component 201 would be inserted at the time the patient would be undergoing a total hip arthroplasty. The utility of the interface 211 would come into play after a periprosthetic fracture was to occur. The insertion of Guide Wire 202 into Modified Femoral Component 201 to facilitate the interface of Cannulated Outrigger 203 would be temporary. This interface can then be uncoupled after fixation of the fracture has occurred through the use of a fracture stabilization component, such as the Modular Plate 204A, B, and C and screw fixation with Screw 206. The pre-engineered geometry in Modified Femoral Component 201 would be done at the time of manufacture of said component. Additionally, the Interface 211 as well as the screw holes for Screw 206 would be incorporated into Component 201 prior to implantation, thus ready to be utilized at a future date should periprosthetic fracture of Native Femur 209 occur after total hip arthroplasty. Necessitates it is inserted into the Modified Femoral Component 201 and around the prosthesis either via screws in a trajectory that does not interfere with the Prosthesis 101 or wires that wrap around the bone properly, providing for a method of fixation that once again does not interfere with Prosthesis 101. It should be noted that this deals with only one specific fracture pattern of the proximal femur below a Hip Prosthesis 101. Other potential fracture patterns do exist around other prosthetic implants which will be addressed in further figures in this document.

Figure 3:
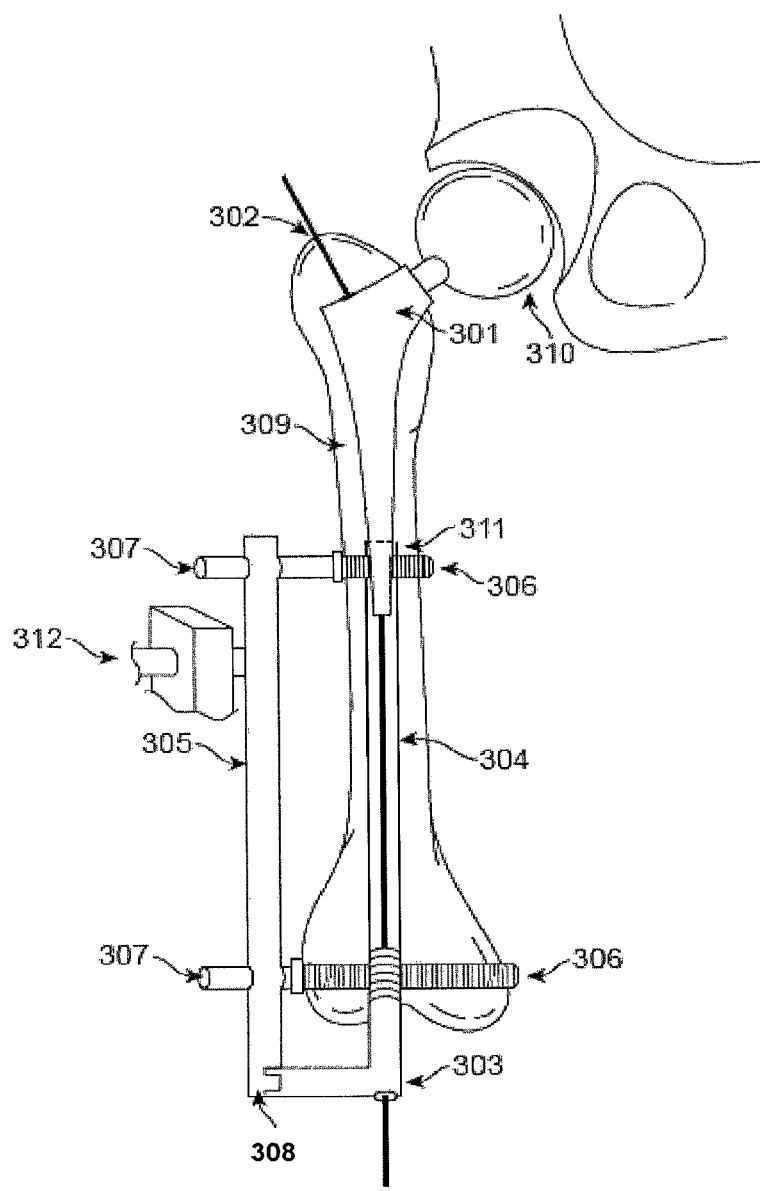
FIG. 3 is an illustration of an embodiment including: Alternative Modified Femoral Component to Accommodate Cannulated Outrigger, Custom Retrograde Nail and Targeting Device.

FIG. 3: Solution #2—Alternative Modified Femoral Component to Accommodate Cannulated Outrigger, Custom Retrograde Nail and Targeting Device FIG. 3 represents an alternative embodiment of the modified femoral component 301 and associated components. This embodiment of the modified femoral component accommodates a custom retrograde Femoral Nail 304 in the treatment of a periprosthetic distal femur fracture. The modified Femoral Component 301 would be inserted at the time of total hip arthroplasty; this component is utilized as a component of fixation of said fracture of the Native Femur 309 after total hip arthroplasty. The Guide Wire 302 is inserted through the Modified Femoral Component 301 which contains an inner cannulation component. The guide wire is advanced to the end of the Native Femur 309 and goes past the fracture site. This guide wire is then be utilized to direct the Custom Retrograde Femoral Nail 304 so that it is placed over the tip of the Modified Femoral Component 301 to provide for an engagement and subsequently secure fracture fixation. The interface between the Modified Femoral Component 301 and the Custom Retrograde Femoral Nail 304 will be further depicted in FIG. 4 which is labeled in the current diagram as 311. Some embodiments will provide for a keyed interface 311 between the Modified Femoral Component 301 and the Custom Retrograde Nail 304. The insertion of the Guide Wire 302 to accommodate and guide the Retrograde Femoral Nail 304 takes place at the time of surgical repair of the fracture. Once the guide wire has been passed to the end of the Native Femur 309 an opening at the distal femur would occur to provide for an entry portal of the Retrograde Femoral Nail 304. Attached to the Retrograde Femoral Nail 304 would be an aligning device, such as the custom Cannulated Outrigger 303. This outrigger is cannulated to accommodate the Guide Wire 302 and the Guide Nail 304 to the appropriate position at the tip of the Customized Modified Femoral Component 301. Attached to 303 will be an aiming arm, such as the Proximal Targeting Device 305. The adjoinment of 305 to 303 would occur at Coupling Point 308. Once an aiming arm, such as the proximal targeting device, is in place it would provide for appropriate and predetermined targeting for the Fixed-Angled Interlocking Screws 306 both at the proximal and distal aspect of the fixation. The screws would align with the fixation device, customized Retrograde Femoral Nail 304, with the use of an aiming arm, such as the proximal targeting device, and the Screw Alignment Cannula 307. A cutaway diagram reveals a three-dimensional profile of an aiming arm, such as Proximal Targeting Device 305, which is labeled 312 in this figure. The benefits of this embodiment provide for a biologically favorable method of fixation that is amenable to minimal soft tissue stripping thus preserving biology around the fracture and helping promote rapid healing. Additionally, surgical time would be significantly shortened. Biomechanical favorability is also achieved with the overlap interface that is obtained between the Customized Modified Femoral Component 301 and the Custom Retrograde Femoral Nail 304. Once again this interface, labeled 311, will be further depicted in the next drawing.

In addition, Modified Femoral Component distal tip 311, may include(in specific embodiments) a specific alignment key feature which allows for alignment of pre-drilled holes which may be present in the Custom Retrograde Femoral Nail 304, and the Modified Femoral Component 301, such that a keying feature angularly aligns with a keying feature present in the Retrograde Femoral Nail 304. One such keying feature may be a notched interface, allowing for proper rotational alignment.

Figure 4:
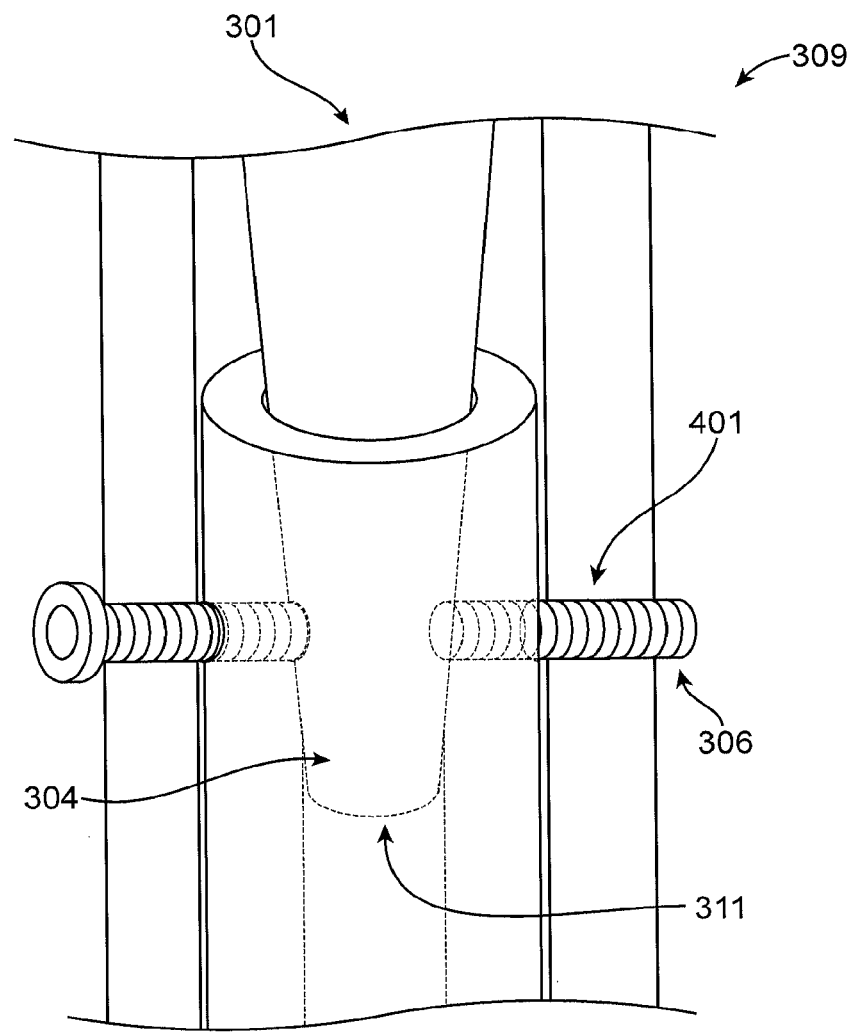
FIG. 4 is an illustration of an embodiment including: Magnified detail of Modified Femoral Component Tip to Accommodate Retrograde Nail.

FIG. 4: Magnified Detail of Modified Femoral Component Tip to Accommodate Retrograde Nail In FIG. 4 the depiction represents the interface on a magnified scale between the Modified Femoral Component 301 and the Custom Retrograde Femoral Nail 304. The interface is further specified as 311. In this depiction, a tapering and smaller diameter at the tip of 301 is designed to provide for a unique and overlapping interface between the Modified Femoral Component 301 and the Retrograde Femoral Nail 304. This overlap helps achieve mechanical stability by preventing a stress riser that would occur if no overlap were to exist. Additionally, a predetermined trajectory would be placed and aligned to accommodate the Angular Stable Interlocking Screw 306. This would interface through the cortical bone depicted as 401 as well as the Custom Retrograde Femoral Nail 304 and the Modified Femoral Component 301 and subsequent Modified Femoral Component Distal Tip 311. The ability to target this screw and align it appropriately would be facilitated through the attachment of an aligning device, such as the Cannulated Outrigger 303 depicted in FIG. 3 along with an aiming arm, such as the Proximal Targeting Device 305 and subsequent Alignment Cannula 307.

Figure 5:
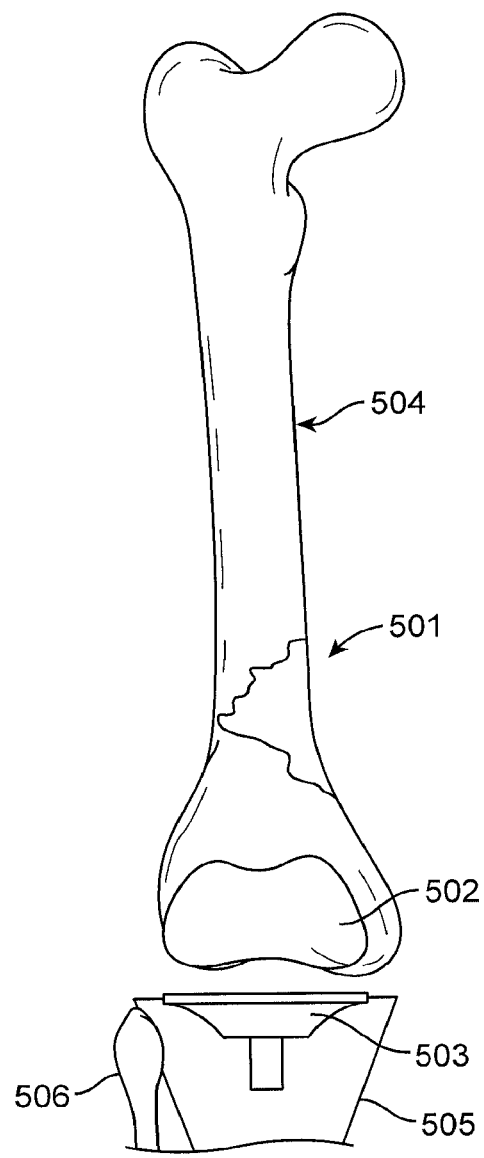
FIG. 5 is an illustration of a periprosthetic distal femur fracture.

FIG. 5: Problem #2—Periprosthetic Distal Femur Fracture Above a Prosthetic Total Knee Arthroplasty.

Depicted in FIG. 5 is the clinical scenario where a fracture would occur above a previously inserted total knee arthroplasty. The fracture would occur in the Native Bone 504 and be depicted by the Fracture Pattern 501. Please note that this is one of potentially many different fracture patterns that may exist and this is only one embodiment of this said fracture. The Femoral Component 502 would be placed onto the Native Femur 504 at the time of total knee arthroplasty.

Similarly, the Tibial Component 305 would be placed into the Native Tibia 505 at the time of total knee arthroplasty to articulate the Femoral Component 502. Additionally depicted is the Native Fibula 506. The clinical problem that will be subsequently discussed will be to address said fracture 501 above a total knee arthroplasty otherwise known as a periprosthetic distal femur fracture.

Figure 6:
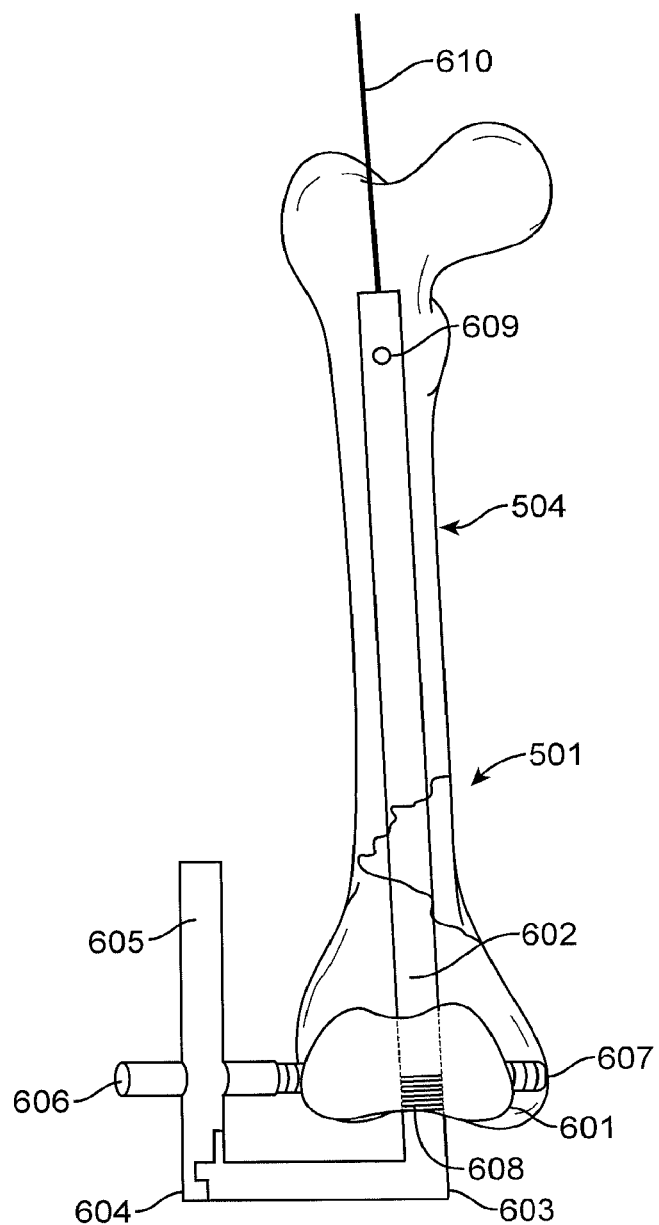
FIG. 6 is an illustration of an embodiment including: Angular Stable Retrograde Periprosthetic Distal Femoral Nail.

FIG. 6: Embodiment of Solution #3—Angular Stable Retrograde Periprosthetic Distal Femoral Nail In an embodiment of one of the current inventions, the alignment devices including the Cannulated Outrigger 603, Proximal Targeting Device 605, Angular Stable Screw Alignment Cannula 606, and Couple Point 604 can be constructed out of a radiolucent material to provide for an avenue of X-ray visualization to help assure appropriate alignment as well as placement. In this embodiment, alignment device required as the prosthetics prevent x-ray imaging and free hand alignment. This is a key advantage and solution to an existing problem. Also note that the alignment device/outrigger may be composed on carbon fiber or other materials transparent to imaging technology using radio lucent materials in some embodiments.

Figure 7:
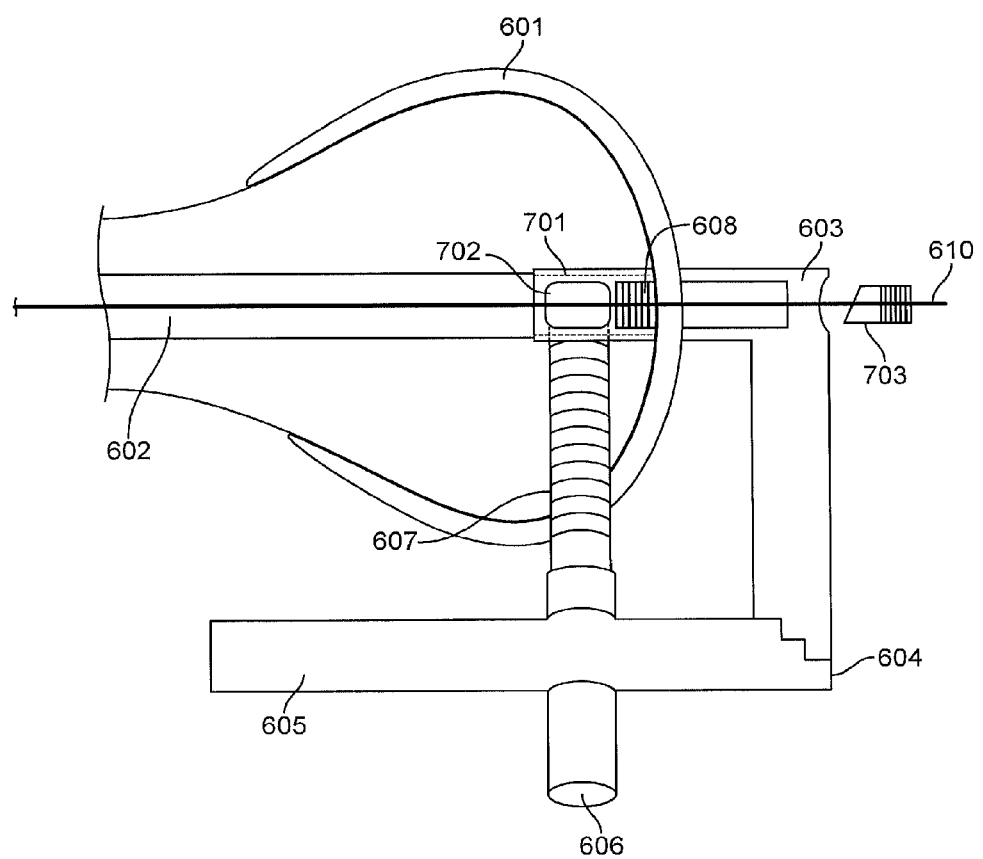
FIG. 7 is an illustration of an embodiment including: Detailed Lateral Projection of Modified Femoral Component (601).

FIG. 7: Detailed Lateral Projection of an Embodiment of a Modified Femoral Component (601)

Depicted in this drawing is a lateral projection of an embodiment of the Modified Femoral Component 601 with the Custom Angular Stable Retrograde Femoral Nail 602 being inserted as would happen in a clinical scenario during fracture repair. The insertion is to the point where the interface is occurring between the Modified Femoral Component 601 and the Custom Retrograde Angular Stable Femoral Nail 602. The alignment as well as insertion would be facilitated over Guide Wire 610 and through the attached Custom Outrigger 603, aiming arm, such as Proximal Targeting Device 605, Alignment Cannula 606, and Coupling Point 604. Depicted out of plane is the Angular Stable Interlocking Screw 607 which would traverse the region labeled 702 and interact with the modification of Modified Femoral Component 601, depicted as 701. The interface and alignment is secured between the Custom Retrograde Femoral Nail 602 and an aligning device, such as the Cannulated Outrigger 603 by a Threaded Interface 608. The design of Subcomponent 601, that is labeled 701, would be made in a way to accept the Retrograde Femoral Nail 602 as well as provide for the traversing of the Angular Stable Interlocking Screw 607. The geometry is designed, as such, to control the coronal and sagittal plane angulatory forces to help maintain alignment. The final capacity to be able to maintain this alignment would be facilitated by the angular stable set assembly end cap with three rotating angular interfaces. Further detail of this object will be described in FIG. 8. Further details around the Area 701, which is specifically described as contingent prosthetic distal femoral nail interface, will be provided. The design of 701 would be manufactured into the Component 601 at the time of initial manufacturing. This modification, 701, would exist at the time of total knee arthroplasty and be present as a contingent source of fixation with angular stabilization should a fracture of the distal femur arise. The geometry of 701, once again, would be to accept the Angular Stable Interlocking Screw 607 as well as the angular stable set assembly end cap with Free Rotating Angular Interface 703. The addition of these two devices through the portal labeled 702 would then be able to obtain and maintain sagittal as well as coronal plane stability. This embodiment encompasses the distinctive benefits of both 703 by itself, and 701 by itself, as well as combined. Further use of 701 as a contingent structure, and separately as a device to accept the nail in operation are further contemplated.

Figure 8:
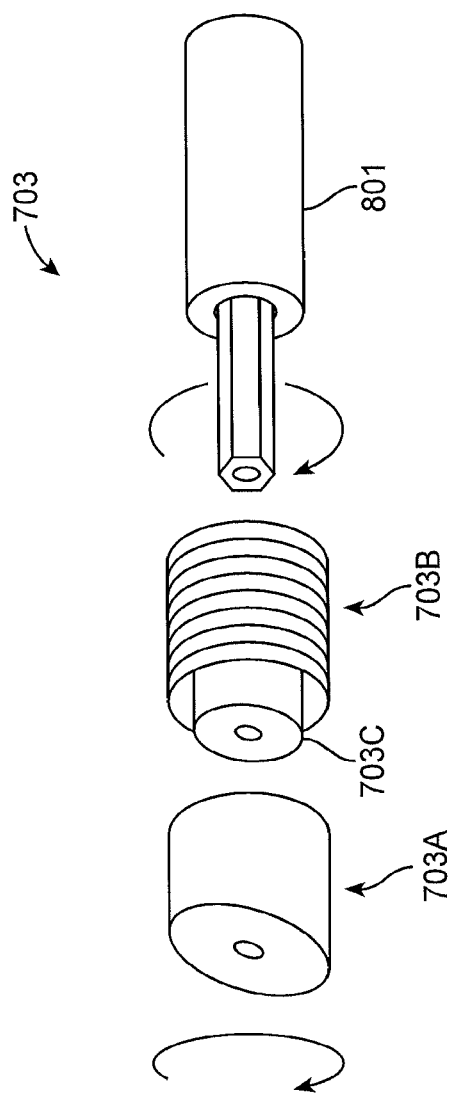
FIG. 8 is an illustration of an embodiment including: Detail of (703) Angular Stable Set Assembly with Free Rotating Angular Interface.

FIG. 8: Detail of an Embodiment of (703) Angular Stable Set Assembly with Free Rotating Angular Interface Depicted in FIG. 8 is a breakdown of an embodiment of the components of the angular stable set assembly end cap with free rotating angular interface. This end cap would be inserted through the Custom Outrigger 603 over the Guide Wire 610. It would then interface through the subcomponent of the Modified Femoral Component 601, labeled as 701. This interface would then provide for a frictional fit to secure the Angular Stable Interlocking Screw 607. Depicted in FIG. 8 is 703A which is the angular portion of the angular state assembly end cap. This is depicted as having a smooth surface to provide for a free-glide insertion without interfacing with underlying threads. Allowing for the insertion would be a Threaded Component 703B. This would interface the threaded component of the Custom Retrograde Femoral Nail 602 at the region labeled 608 in FIG. 7. The threaded capability of this component provides for a threaded and locked frictional fit to secure the interface between Subcomponent 703 of the angular stable set assembly with free rotating angular interface and the Angular Stable Interlocking Screw 607. Free rotation of this device would be allowed through the interface containing a smaller diameter to engage, labeled 703C. The entire Assembly 703A, 703B, and 703C, once placed over the Guide Wire 610, would be screwed into position using the Cannulated Screwdriver 801.

Figure 9:
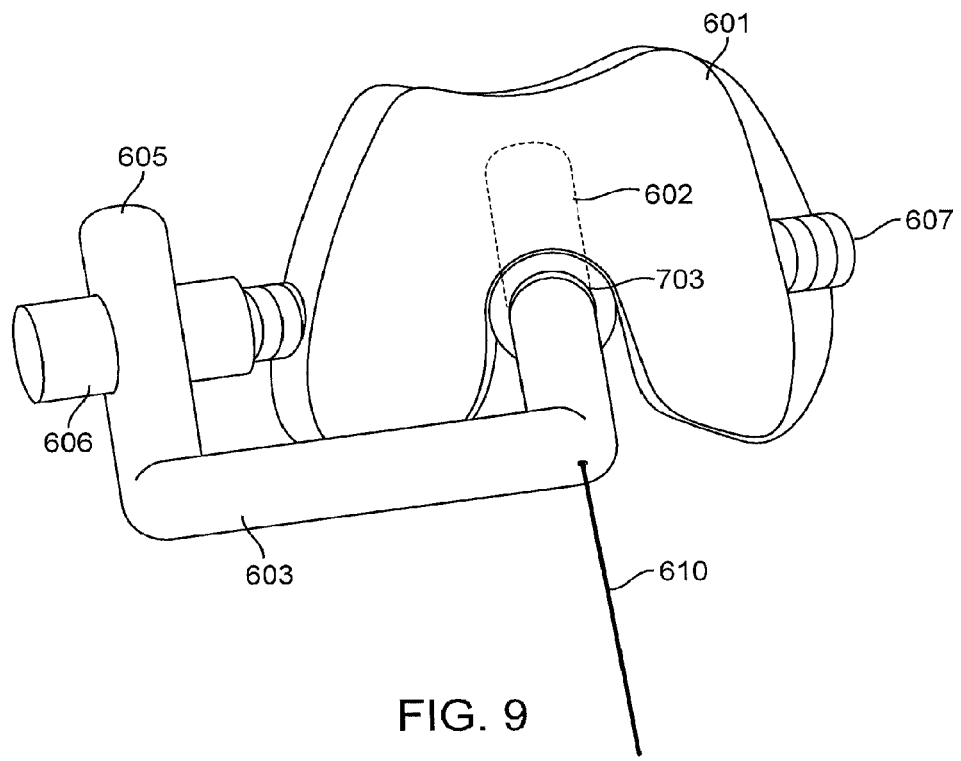
FIG. 9 is an illustration of an embodiment including: Distal Axial Projection of FIG. 6: Angular Stable Retrograde Periprosthetic Distal Femoral Nail.

FIG. 9—Distal Axial Projection of FIG. 6 and an Embodiment of an Angular Stable Retrograde Periprosthetic Distal Femoral Nail Depicted in FIG. 9 is an embodiment of the current invention including an axial projection viewing the innerconnular region of the Modified Femoral Component 601. Once the Retrograde Femoral Nail 602 is inserted through the inner-connular notch over Guide Wire 601, and facilitated by an aligning device, such as the Cannulated Outrigger 603, an Angular Stable Interlocking Screw 607 would then be inserted. This insertion would be introduced with the Alignment Cannula 606 and placed through an aiming arm, such as the Proximal Targeting Device 605. The interface would occur at the modified subcomponent of Modified Femoral Component 601, labeled 703. The projection of 703 in this diagram is a combination of 701 and 702 from FIG. 7. The purpose of this depiction is to demonstrate that no alteration of the surface of the Modified Femoral Component 601 would occur at the time that the fracture fixation would take place, using the insertion of Modified Retrograde Femoral Nail 602 and the placement of Angular Stable Interlocking Screw 607.

Figure 10:
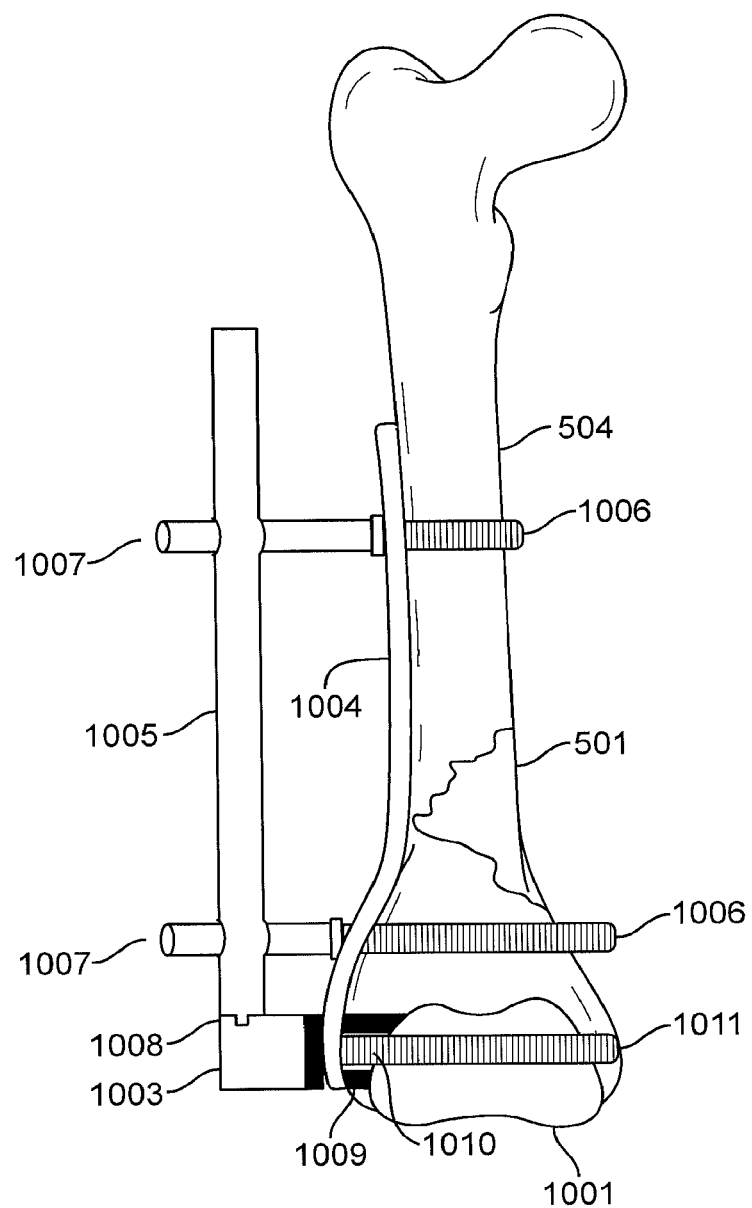
FIG. 10 is an illustration of an embodiment including: Distal Femoral Periprosthetic Plate Fixation with contingent prosthetic interface.

FIG. 10: Solution #4—Distal Femoral Periprosthetic Plate Fixation with Contingent Prosthetic Interface Depicted in this diagram is an alternative embodiment of a method of fixation to deal with a periprosthetic distal femoral fracture. This fracture would be of Native Bone 504 and is depicted as Fracture Pattern 501. The Modified Femoral Component 1001 would be placed at the time of total knee arthroplasty. Modifications would be in place at the time of manufacture of Modified Femoral Component 1001 and be available for a contingent fracture fixation should Fracture 501 occur after total knee arthroplasty takes place. The Modified Femoral Component 1001 is further described as a modified femoral component that interfaces with custom angle stable periprosthetic distal femoral, polyaxial locking plate. In FIG. 10, the Distal Plate Outrigger 1003 is shown to connect to the Custom Angular Stable Periprosthetic Distal Femoral Polyaxial Locking Plate 1004 through the 1003/1001 custom interface—prosthetic contingent mounting interface. Through Couple Point 1008 Proximal Targeting Device 1005 is depicted providing for cannula placement for Screw Alignment Cannula 1007. Through 1007 there would be placed some Fixed Angled Locking Screws 1006 which would interface and subsequently thread into Plate 1004. Distally, once 1009 prosthetic contingent mounting interface is installed to 1004 as well as 1001, the predetermined alignment would be allowed for the placement of Central Distal Angular Stable Interlocking Screw 1011 through the Central Distal Angular Stable Screw Portal 1010.

This alternative embodiment of fixation for Distal Femoral Fracture 501 utilizes a plate-and-screw construct to achieve axial, sagittal, as well as coronal plane alignment maintenance. The capacity to interface with Modified Femoral Component 101 allows for no reliance upon the integrity of the Distal Femoral Bone 504, but rather the ability to directly interface and adjoin to Modified Femoral Component 101 so as to maintain above-said alignments in all three planes. Fracture fixation and alignment is also further maintained with the insertion of additional Locking Screws 1006 above and below the Periprosthetic Fracture 501. The clinical advantage of this device once again provides for minimally invasive exposure of the distal femur and soft tissue preservation for enhanced biologic preservation around Fracture Site 501. Aiming arm, such as the Proximal Targeting Device 1055 would reside outside the skin of the soft tissue envelope of the Femur 504 and guide 1007, screw alignment cannula, through the skin to align appropriately with the Custom Angular Stable Periprosthetic Distal Femoral Polyaxial Locking Plate 1004. Screws would then be inserted through the Plate 1004 and Underlying Bone 504 and lock into position.

Figure 11:
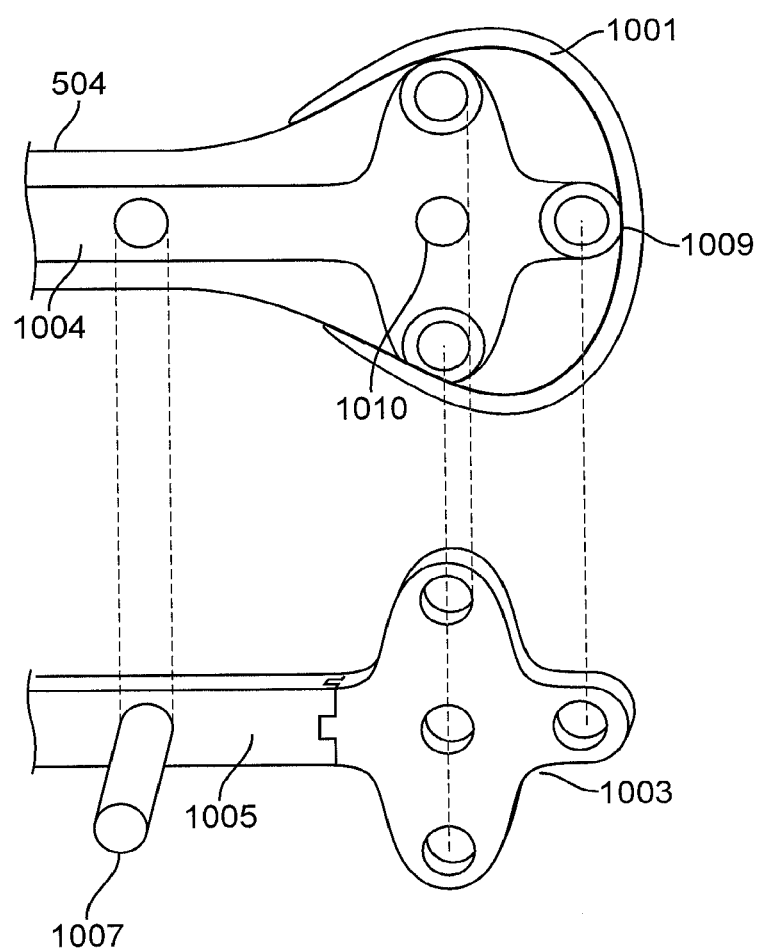
FIG. 11 is an illustration of an embodiment including: Lateral Projection of Distal Femoral Periprosthetic Plate Fixation with contingent prosthetic interface.

FIG. 11: Lateral Projection of an Embodiment of a Distal Femoral Periprosthetic Plate Fixation with Contingent Prosthetic Interface This figure details an embodiment of the three-phase interface between Modified Femoral Component 1001, the custom angular stable periprosthetic distal femoral plate and the Distal Femoral Outrigger 1003. Depicted in 1009 is the interface that allows for the adjoining of 1003 to Modified Femoral Component 1001 as well as the Interposed Plate 1004. The ability to interface all three components provides for the ability to specifically target an angular stable interlocking screw depicted as 1011 in FIG. 10. With the adjoining of these components a fixed-angled construct would exist between the Modified Femoral Component 1001 and the Custom Angular Stable Plate 1004; thus being able to achieve the maintenance of axial, sagittal, as well as coronal plane alignment and avoid the reliance upon underlying native bone quality. Additionally depicted is a Central Pole 1010 that would accommodate a large central angular stable interlocking screw for additional fixation. This screw may be placed in a polyaxial locking capacity. Of note, is the modifications of the Distal Femoral Component 1001 to accommodate the adjoining interface to Custom Angular Stable Locking Plate 1004 and the modifications to Modified Femoral Component 601 to accommodate the Custom Retrograde Femoral Nail 602 can be made within the same implant. With both options available for either plate or nail fixation, a variety of different fixation strategies can be accommodated by the same Modified Femoral Component. Once again, these modifications would take place at the time of manufacture of the Modified Femoral Component 601/1001 and not interfere with the articulation of the planned total knee arthroplasty. The contingencies would remain in place and provide for fixation options should a distal femoral fracture depicted as 501, occur.

1009 allows for the joining of the 1003 outrigger to 1004 plate, and additionally provides for the joining of 1001 femoral component to 1004 plate.

In one embodiment, a screw is used to mount the outrigger, through the plate's holes top the prosthetic. 1009 allows for the joining of the 1003 outrigger to 1004 plate, and additionally provides for the joining of 1001 femoral component to 1004 plate. In one embodiment screws are used to mount the outrigger, through the plate's holes on top of the prosthetic. In this embodiment, several novelties in the prosthetic include contingent accommodations for femoral fracture management procedures, and further the specifics of those accommodations and their use at the time of the repair, and the details of the attached devices and methods for using the features provided.

Figure 12:
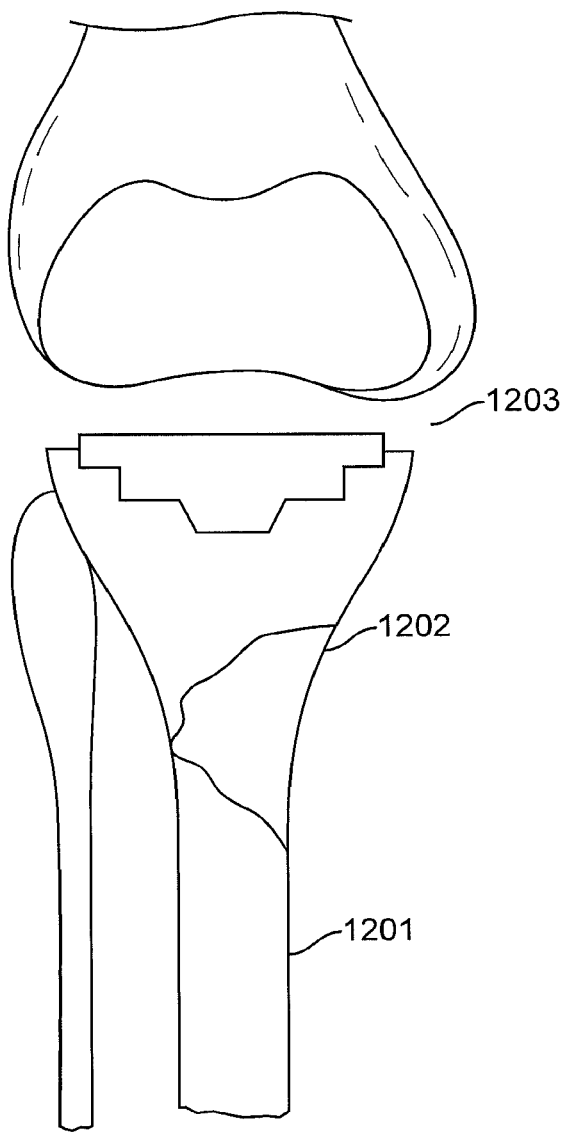
FIG. 12 is an illustration including: a fracture below the tibial tray.

FIG. 12: Problem #3—Fracture Below Tibial Tray

Depicted in FIG. 12 is the Native Tibia 1201 as well as potential future fracture of the proximal tibia, labeled 1202. Please note that the Fracture Pattern 1202 is only one potential fracture pattern that could exist below the tibial tray component of the total knee arthroplasty. The tibial tray component is labeled in this diagram as 1203.

Figure 13:
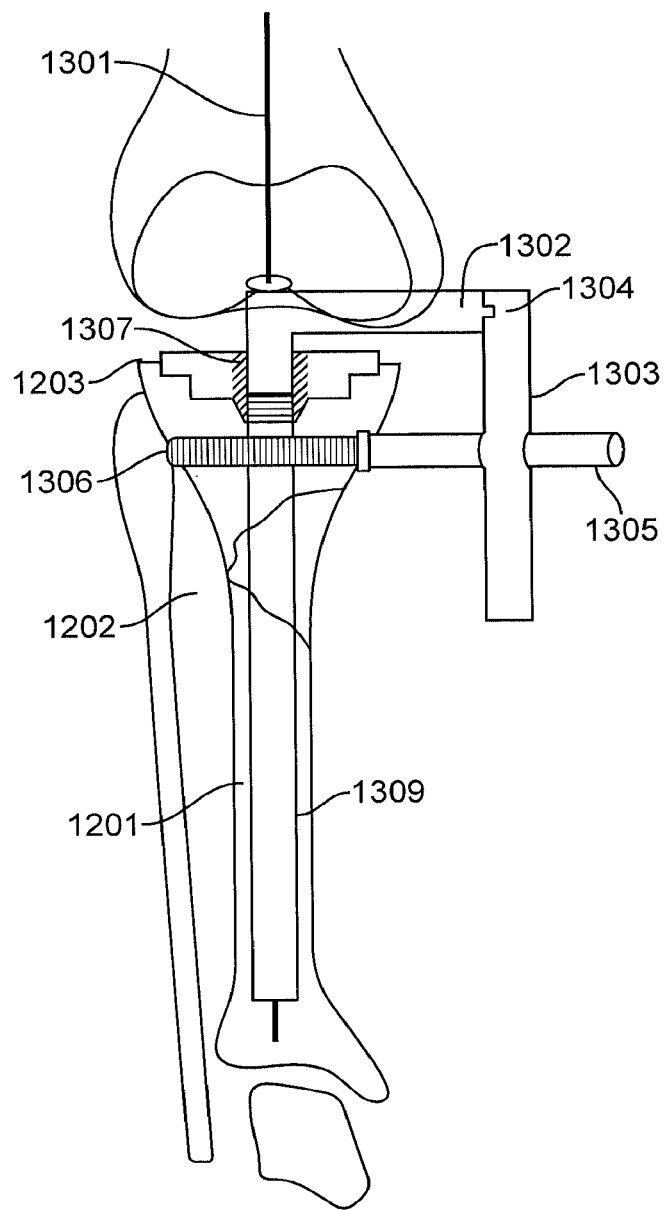
FIG. 13 is an illustration of an embodiment including: Modified Tibial Tray to accommodate contingent fracture management.

FIG. 13: Solution #5—Modified Tibial Tray to Accommodate contingent fracture Management Depicted in FIG. 13 is one embodiment of the fracture management device to address fracture of a Tibial Component 1203 with the fracture depicted as 1202. A Guide Wire 1301 would be inserted at the time of fracture fixation through the Tibial Component 1203 through the Interface 1307. Over this guide wire would be placed a Tibial Nail Fixation Device 1309 with the insertion of 1309 being facilitated through an aligning device, such as a Cannulated Outrigger 1302 and aiming arm, such as Proximal Targeting Device 1303. Further details of a coupling point between 1302 and 1303 are depicted as 1304. Providing for appropriate targeting and placement of the Fixed-Angled Locking Screw 106 would be the Screw Alignment Cannula 1305 inserted through the Proximal Targeting Device 1303. The advantage of this design provides for medullary fixation of the fracture of the Native Tibia 1201 with the fracture pattern depicted as 1202. The ability to have the Contingent Prosthetic Accommodation Portal 1307 be in place prior to the fracture provides a significant clinical advantage for potential fracture fixation. The biomechanical and biological advantages of medullary fixation for a fracture pattern depicted as 1202 of the Native Tibia Bone 1201 are extensive. Ease of operation, maintenance of the current total knee arthroplasty, as well as preservation of biology are all distinct advantages. The addition of biomechanical favorability with the medullary implant is also noted.

Figure 14:
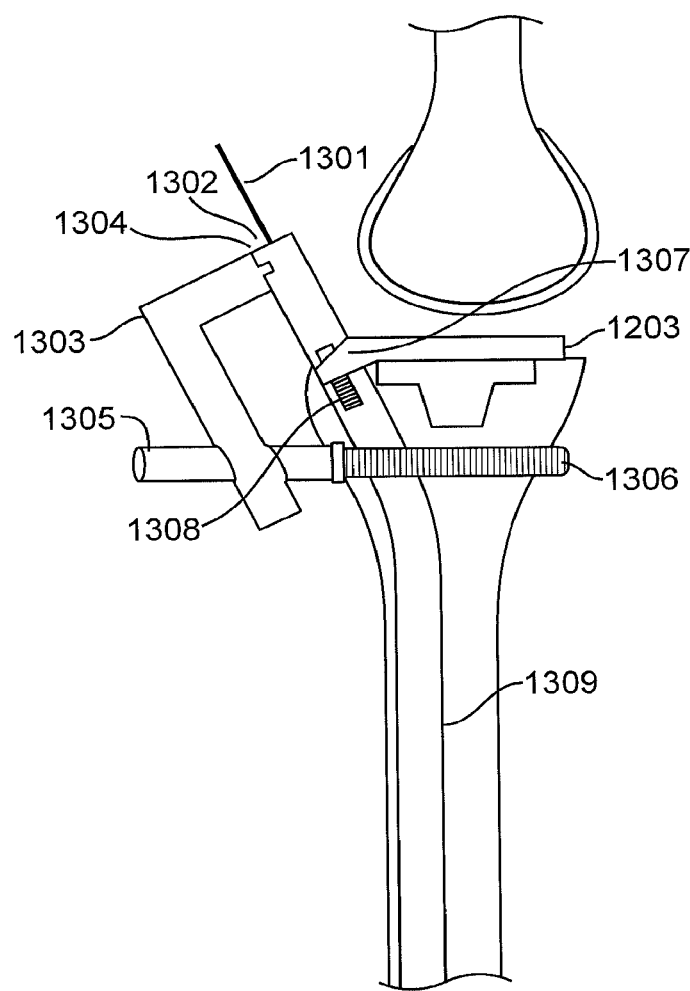
FIG. 14 is an illustration of an embodiment including: Lateral Projection of (FIG. 13) Modified Tibial Tray to accommodate contingent fracture management.

FIG. 14 Lateral Projection of (FIG. 13) Modified Tibial Tray to Accommodate Contingent Fracture Management FIG. 14 represents a Lateral Projection of (FIG. 13) an embodiment of Modified Tibial Tray to accommodate contingent fracture management. Through this lateral projection the Modified Tibial Nail 1309 is inserted through the Customized Tibial Prosthetic Tray 1203 through the Interface 1307. The nail is inserted over a Guide Wire 1301 with this insertion facilitated by an aligning device, such as the Cannulated Outrigger 1302 as well as Proximal Targeting Device 1303. By interlocking the screw 1306 alignment is assured through the Alignment Cannula 1305, with Interlocking Screw 1303 being placed utilizing this mechanism.

To secure fixation between the Tibial Nail 1309 and the Tibial Tray 1203 with this Contingent Prosthetic Accommodation Interface 1307 is a Cannulated Coupling Interface 1308. This interface would provide for fixation between 1309 and 1203. As with the previous devices, the modification to the Tibial Tray 1203 would occur at the time of manufacture and be present as a contingent fixation option should a fracture of Native Tibia Bone 1201 occur in a fracture pattern depicted as 1202.

Figure 15:
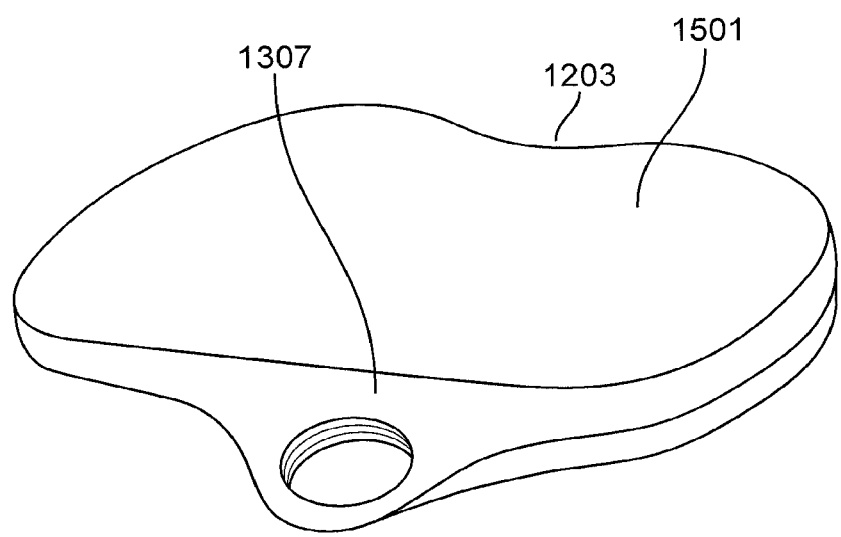
FIG. 15 is an illustration of an embodiment including: 2D rendition of (1203) Prosthetic Tibial Tray.

FIG. 15 2D Rendition of (1203) Embodiment of a Prosthetic Tibial Tray

FIG. 15 represents a three-dimensional projection of an embodiment of the Prosthetic Tibial Tray 1203 with the Contingent Prosthetic Accommodation Portal 1307. Of note there is no modification to the articulating surface of 1203 depicted as 1501.

Figure 16:
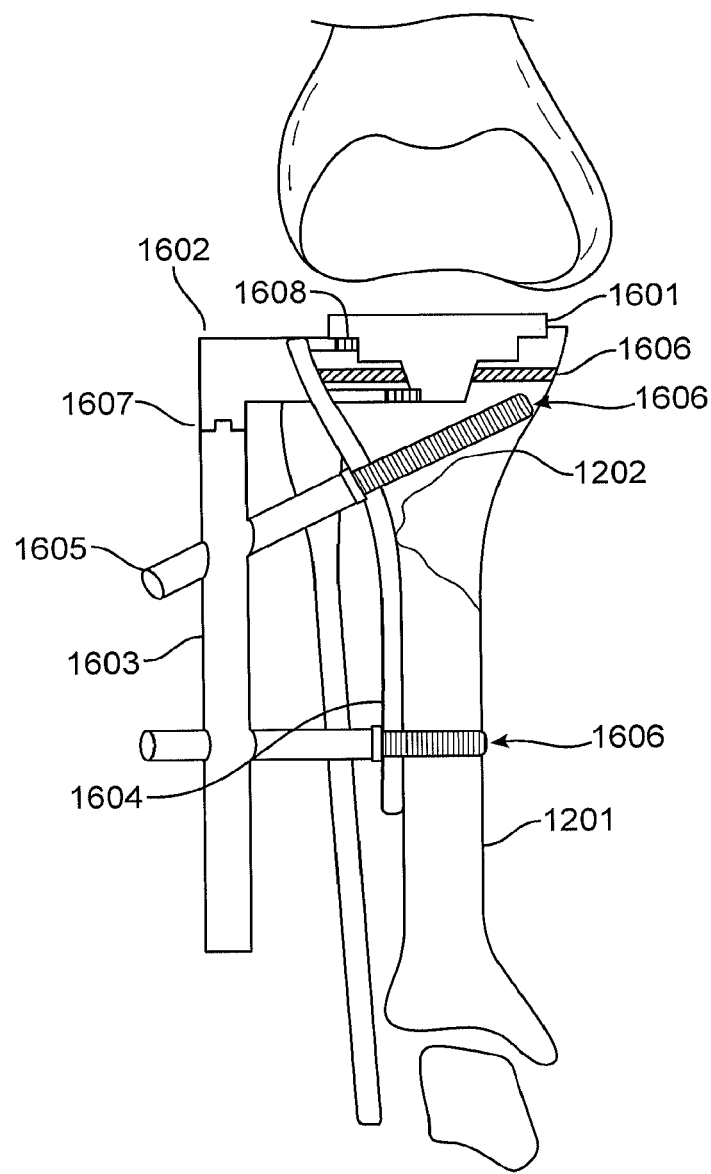
FIG. 16 is an illustration of an embodiment of Contingent Prosthetic Tibial tray accommodation for Proximal Tibial Locking Plate for management of Periprosthetic fracture management.

FIG. 16—Embodiment of Contingent Prosthetic Tibial Tray Accommodation for Proximal Tibial Locking Plate for Management of Periprosthetic Fracture Management Depicted in FIG. 16 is an alternative embodiment of fixation for fracture of the Native Bone 1201, depicted as Fracture Pattern 1202. The placement of the Tibial Tray 1201 would take place at the time of total knee arthroplasty. Fracture below the tibial tray, depicted as 1202, would occur and fixation of said fracture would be managed through the modification of the Tibial Tray 1201. The modifications in Tibial Tray 1201 are made to provide for the adjoining of Custom Outrigger 1602 that would thread into the Modified Tibial Tray 1601 at the Prosthetic Contingent Mounting Interface 1608. This would be through the plate labeled 1604. All three components, 1602, 1604, and 1601 would thus be intimately joined together to provide for appropriate targeting and fixation of Screws 1606. Attached to Proximal Plate Outrigger 1602 would be an aiming arm, such as Distal Targeting Device 1603 that adjoins 1602 through Coupling Point 1607. Through the Distal Targeting Device 1603 Alignment Cannulae 1605 are placed to align the trajectory of the Interlocking Screws 1606.

A distinct clinical advantage for the capacity to align and subsequently maintain the interface between the Tibial Fixation Plate 1604 and the Modified Tibial Tray 1601 relates to the capacity to maintain axial, sagittal, as well as coronal plane alignment both above and below fracture of the Native Tibia 1201, depicted as Fracture Pattern 1202. The plate is designed to be placed in a minimally invasive fashion to avoid compromise of the biology around Fracture 1202. Further clinical advantage is noted by the decrease in surgical time with predetermined targeting as well as enhanced biomechanical properties with the intimate association between the Tibial Plate 1604 and Modified Tibial Tray 1601.

Figure 17:
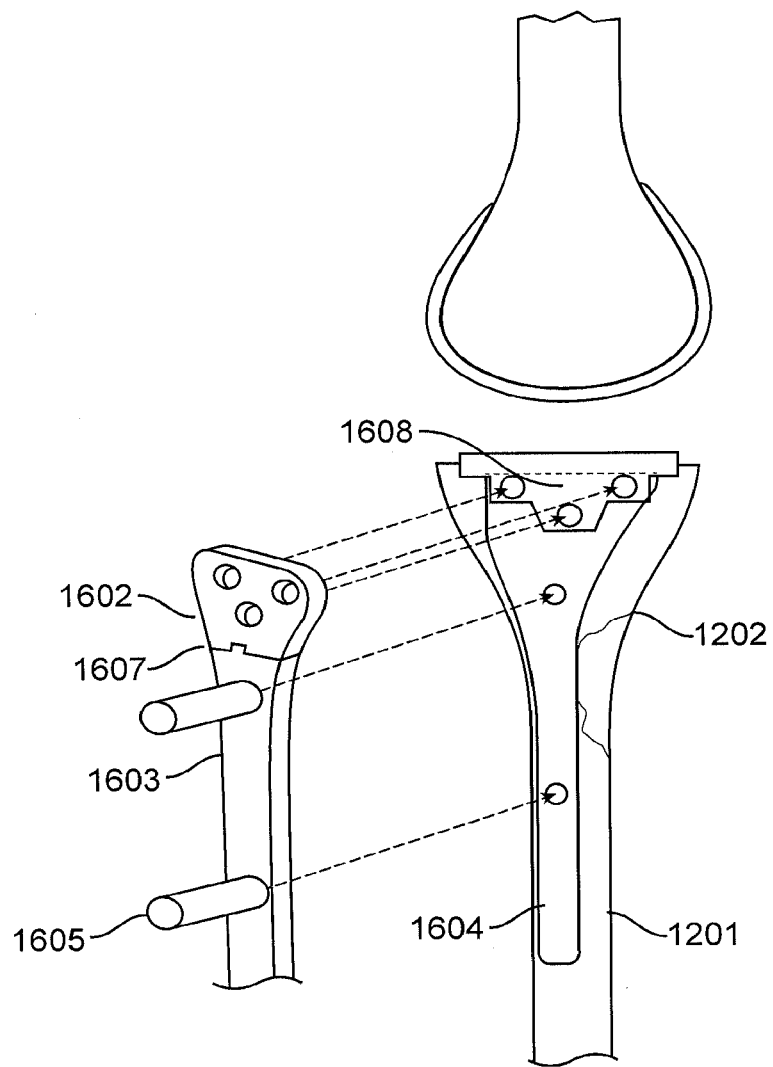
FIG. 17 is an illustration of a Lateral Rendition of (FIG. 16) an embodiment of Contingent Prosthetic Tibial tray accommodation for Proximal Tibial Locking Plate for management of Periprosthetic fracture management.

FIG. 17: Lateral Rendition of (FIG. 16) an Embodiment of Contingent Prosthetic Tibial Tray Accommodation for Proximal Tibial Locking Plate for Management of Periprosthetic Fracture Management A lateral projection depicted in FIG. 17 reveals further detail as to the interface between the Underlying Modified Tibial Tray 1601, Tibial Fixation Plate 1604, as well as the Proximal Plate Outrigger 1602 and aiming arm, such as Proximal Targeting Device 1603. This interface allows adjoinment of the tibial fixation plate directly to the Modified Tibial Tray 1601 at the Interface 1608. This adjoinment is facilitated through the placement of Angular Stable Interlocking Screws 1606. The placement being targeted through the Proximal Plate Outrigger 1602 as well as aiming arm, such as Proximal Targeting Device 1603 and cannulae 1605. With the intimate association between Tibial Tray 1601 and Tibial Fixation Plate 1604, the maintenance of axial, sagittal, as well as coronal alignment is assured.

Figure 18:
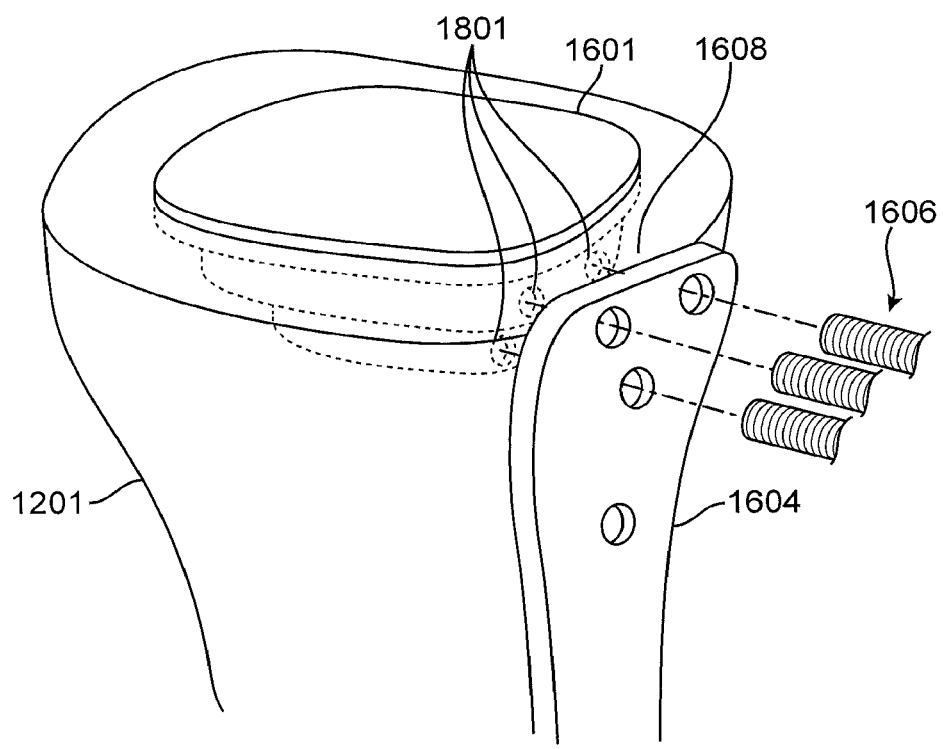
FIG. 18 is an illustration of an embodiment of Tibial Contingent Accommodation and Mounting of Tibial Plate.

FIG. 18: Detail of an Embodiment of Tibial Contingent Accommodation and Mounting of Tibial Plate In FIG. 18 a three-dimensional depiction of an embodiment of the tibial plate fixation device is noted. The Modified Tibial Tray Component 1601 would interface with Tibial Fixation Plate 1604 through the region depicted as 1608. Tibial Tray Contingent Plate Accommodation Mounting Holes 1801 would be present at the time of manufacture. The Tibial Tray Component 1601 would be placed at the time of total knee arthroplasty. Contingent Mounting Holes 1801 would be in place and available to be utilized for fracture fixation should the need arise. These mounting holes would accommodate the Angular Stable Locking Screw 1606 placed to provide for an interface and secure adjoining of Tibial Fixation Plate 1604 to Tibial Tray Component 1601 through Mounting Holes 1801. This mounting interface further assures the maintenance of axial, sagittal, as well as coronal plane alignment. The Tibial Tray Contingent Plate Accommodation Mounting Holes are labeled 1801.

All of the above-described embodiments of devices provide for a variety of fracture fixation options should a fracture occur after total hip arthroplasty or total knee arthroplasty. The current state of fixation of above-said fracture revolves around devices that are designed to avoid originally placed femoral or tibial components. The ability to pre-engineer fracture fixation contingent solutions into femoral or tibial components provides for a distinct clinical advantage in the planning and execution for periprosthetic fracture fixation. With a multitude of different fracture patterns that could clinically exist, current solutions for the variability of fracture patterns revolve around the use of either an external bone plate or an internal medullary rod/nail. None of the devices that currently exist have a pre-engineered solution to intimately associate with the previously placed total hip arthroplasty or total knee arthroplasty. The Proximal Tibial Plate Contingent Mounting Holes 1801 would be in place and present at the time of manufacture. The Tibia fixation plate and further the Tibial Tray Modification 1307 Entry Portal 13 below said component. This component being labeled the further construct ability the depiction of the in the FIG. 8 as well as 503 would be inserted at the time a total knee arthroplasty would be performed.

Note that the provided descriptions of embodiments are for example purposes only to aid in the understanding of the use of the invention. The provided embodiments, figures and discussion should not be construed as limiting the scope or application of the invention contained herein. There are variations and modification to the specific embodiments described which are intended to be included within the scope of this invention.

It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein. The invention has been described in relation to particular examples, which are intended in all respects to be illustrative rather than restrictive. Those skilled in the art will appreciate that many different combinations of hardware, software, and firmware will be suitable for practicing the present invention. Various aspects and/or components of the described embodiments may be used singly or in any combination. It is intended that the specification and examples be considered as exemplary only, with a true scope and spirit of the invention being indicated by the claims.

While this invention has been particularly shown and described with references to example embodiments thereof, it will be understood by those skilled in the art that various changes in form and details may be made therein without departing from the scope of the invention encompassed by the appended claims.

What is claimed is:

1. A prosthesis comprising:
a joint interface surface, configured to articulate in situ against a second joint interface surface of a companion joint structure;
one or more contingent features integrally disposed on or within the prosthesis; and
a removable contingent component interfaced with at least one of the contingent features,
wherein the removable contingent component is arranged to be removable so as to both:
provide access for insertion of a fracture stabilization component within a medullary canal of a bone in which the prosthesis is configured to reside; and
expose the one or more contingent features for use in securing the fracture stabilization component with the prosthesis.

2. The prosthesis of claim 1, wherein the removable contingent component is further for use in securing an aligning arm in mechanical registration with both the prosthesis and the fracture stabilization component.

3. The prosthesis of claim 2, wherein the securing the aligning arm in mechanical registration with both the prosthesis and the fracture stabilization component, is for further use in aligning one or more screws with holes in the prosthesis.

4. The prosthesis of claim 2, wherein the securing the aligning arm in mechanical registration with both the prosthesis and the fracture stabilization component, is for further use in aligning one or more screws with holes in both the fracture fixation component and the prosthesis.

5. The prosthesis of claim 1, wherein the prosthesis is a modified femoral component, and wherein the modified femoral component interfaces with a periprosthetic distal femoral locking plate.

6. The prosthesis of claim 5, wherein the periprosthetic distal femoral locking plate is a polyaxial distal femoral locking plate.

7. The prosthesis of claim 1, wherein the prosthesis includes a modified tibial tray component.

8. The prosthesis of claim 1, wherein at least one of the removable contingent components includes one or more interfaces of the prosthesis.

9. The prosthesis of claim 1, wherein the joint interface surface is notched or keyed for rotational alignment in situ.

10. The prosthesis of claim 1 wherein the one or more contingent features include one or more of a pre-engineered notched interface, a pre-engineered threaded interface or a pre-engineered keyed interface.

11. The prosthesis of claim 1, wherein the one or more contingent features are further configured to be located adjacent to a terminal end and within an outer surface layer of a bone within which the prosthesis resides when in situ.

12. A prosthesis comprising:
a joint interface surface, configured to articulate in situ against a second joint interface surface of a companion joint structure;
one or more contingent features integrally disposed on or within the prosthesis; and
one or more removable contingent components interfaced with at least one of the contingent features,
wherein at least one of the removable contingent components is arranged to be removable in situ so as to expose at least one of the contingent features for use in both:
securing a fracture stabilization component with the prosthesis; and
securing an aligning arm in mechanical registration with both the prosthesis and the fracture stabilization component.

13. The prosthesis of claim 12, wherein the at least one removable contingent component for securing the aligning arm in mechanical registration with both the prosthesis and the fracture stabilization component, is further for use in aligning one or more screws with holes in the fracture stabilization component.

14. The prosthesis of claim 12, wherein the securing the aligning arm in mechanical registration with both the prosthesis and the fracture stabilization component, is for further use in aligning one or more screws with holes in the prosthesis.

15. The prosthesis of claim 12, wherein the securing the aligning arm in mechanical registration with both the prosthesis and the fracture stabilization component, is for further use in aligning one or more screws with holes in both the fracture stabilization component and the prosthesis.

16. The prosthesis of claim 12, wherein the prosthesis is a modified femoral component, and wherein the modified femoral component interfaces with a periprosthetic distal femoral locking plate.

17. The prosthesis of claim 16, wherein the periprosthetic distal femoral locking plate is a polyaxial distal femoral locking plate.

18. The prosthesis of claim 12, wherein the prosthesis includes a modified tibial tray component.

19. The prosthesis of claim 12, wherein at least one of the removable contingent components includes one or more interfaces of the prosthesis.

20. The prosthesis of claim 12, wherein the joint interface surface is notched or keyed for rotational alignment in situ.

21. The prosthesis of claim 12 wherein the one or more contingent features include one or more of a pre-engineered notched interface, a pre-engineered threaded interface or a pre-engineered keyed interface.

22. The prosthesis of claim 12, wherein the one or more contingent features are further configured to be located adjacent to a terminal end and within an outer surface layer of a bone within which the prosthesis resides when in situ.

* * * * *